(12) United States Patent
Lutz et al.

(10) Patent No.: US 9,277,974 B2
(45) Date of Patent: Mar. 8, 2016

(54) DENTAL IMPLANT

(75) Inventors: Walter Lutz, Wertheim (DE); Stefan Ries, Wertheim (DE)

(73) Assignee: Cera M GmbH, Wertheim (DE)

( * ) Notice: Subject to any disclaimer, the term of this patent is extended or adjusted under 35 U.S.C. 154(b) by 89 days.

(21) Appl. No.: 13/520,697

(22) PCT Filed: Dec. 10, 2010

(86) PCT No.: PCT/EP2010/007537
§ 371 (c)(1),
(2), (4) Date: Oct. 1, 2012

(87) PCT Pub. No.: WO2011/069671
PCT Pub. Date: Jun. 16, 2011

(65) Prior Publication Data
US 2013/0017513 A1    Jan. 17, 2013

(30) Foreign Application Priority Data
Dec. 10, 2009   (DE) .......................... 10 2009 057 754

(51) Int. Cl.
*A61C 13/00*    (2006.01)
*A61C 8/00*    (2006.01)

(52) U.S. Cl.
CPC .............. *A61C 8/005* (2013.01); *A61C 8/0066* (2013.01); *A61C 8/0069* (2013.01); *A61C 8/0059* (2013.01); *A61C 8/0063* (2013.01)

(58) Field of Classification Search
USPC ................................................. 433/172–176
See application file for complete search history.

(56) References Cited

U.S. PATENT DOCUMENTS

| | | | |
|---|---|---|---|
| 8,597,023 B2* | 12/2013 | Zipprich et al. | 433/173 |
| 2003/0104336 A1* | 6/2003 | Sethi et al. | 433/141 |
| 2008/0182227 A1* | 7/2008 | Wolf et al. | 433/174 |
| 2008/0261176 A1* | 10/2008 | Hurson | 433/174 |
| 2009/0123889 A1* | 5/2009 | Mehrhof | 433/173 |
| 2009/0239196 A1* | 9/2009 | Lerner et al. | 433/174 |
| 2010/0311014 A1* | 12/2010 | Garcia Saban et al. | 433/174 |

FOREIGN PATENT DOCUMENTS

| | | | |
|---|---|---|---|
| DE | 102007013603 | 9/2008 | |
| EP | 1529498 | 5/2005 | |
| EP | 1529498 A1 * | 5/2005 | ............... A61C 8/00 |
| EP | 1728486 | 12/2006 | |
| WO | 2006/035011 | 4/2006 | |
| WO | WO2008155135 A1 * | 12/2008 | ............... A61C 8/00 |
| WO | WO 2009068699 A1 * | 6/2009 | ............... A61C 8/00 |

* cited by examiner

*Primary Examiner* — Yogesh Patel
(74) *Attorney, Agent, or Firm* — Dilworth & Barrese, LLP.

(57) ABSTRACT

A dental implant comprises an implant screw (1) with an external thread (5), an implant abutment (3) and a tightening screw (4) which can be screwed into the implant screw (1) and by which the implant abutment (3) is connectable or connected with the implant screw (1), wherein the implant screw (1) rests against a contact surface (14, 15) of the implant abutment (3) with a contact surface (10, 11). To improve such dental implant, the implant screw (1) and the implant abutment (3) are made of a ceramic material at least in the region of their contact surfaces (10, 11; 14, 15). The contact surface (14, 15) of the implant screw (1) and the contact surface (14, 15) of the implant abutment (3) are ground in against each other.

13 Claims, 4 Drawing Sheets

Fig. 2
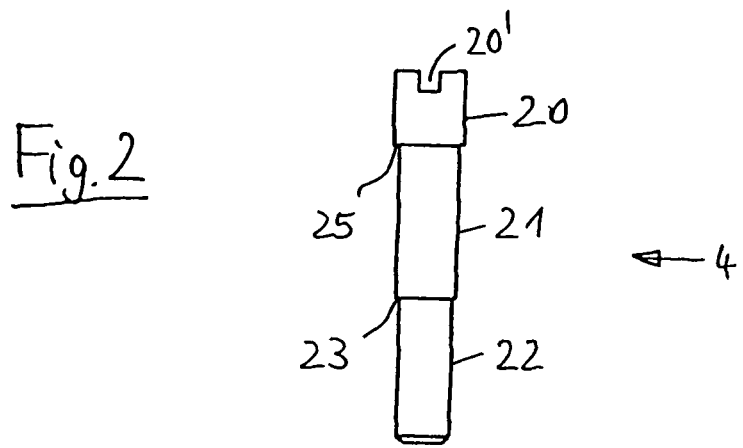
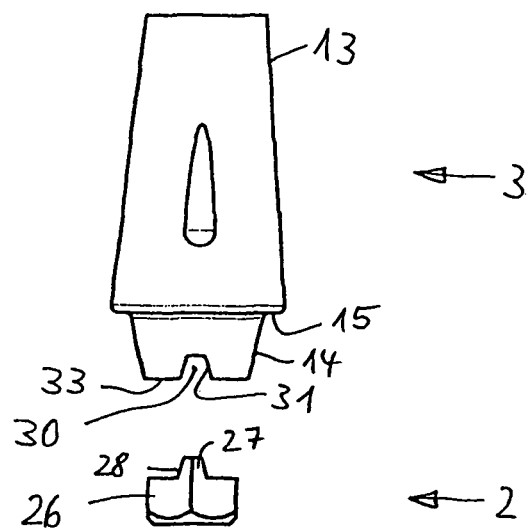
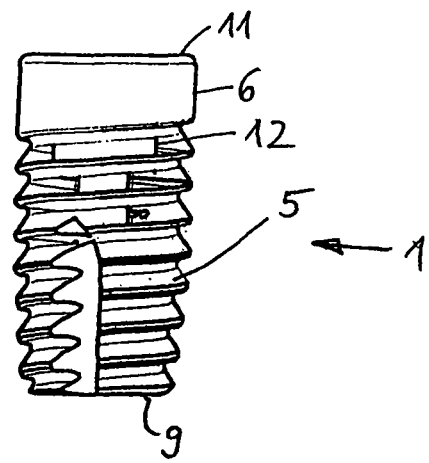

Fig. 3
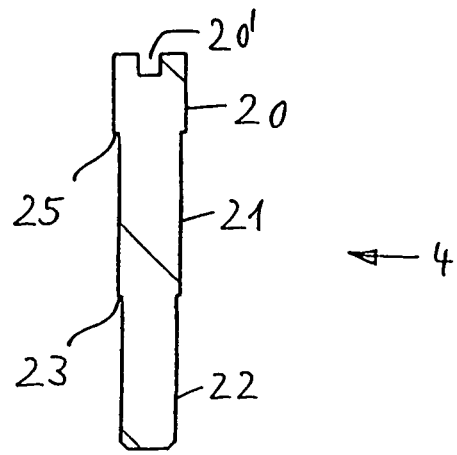
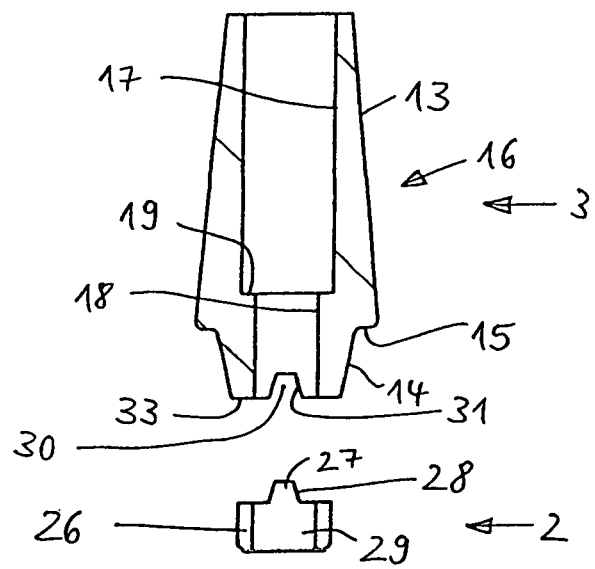
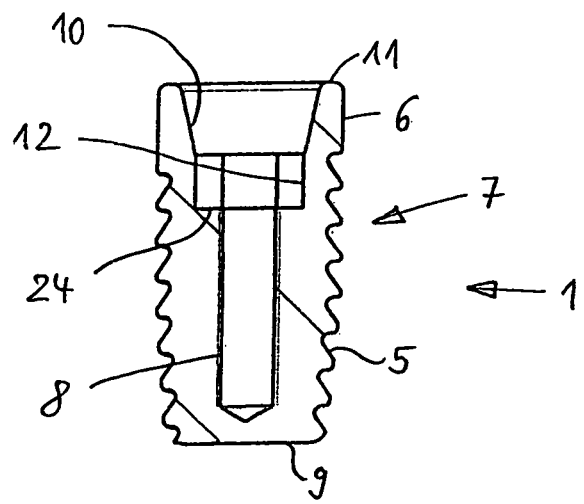

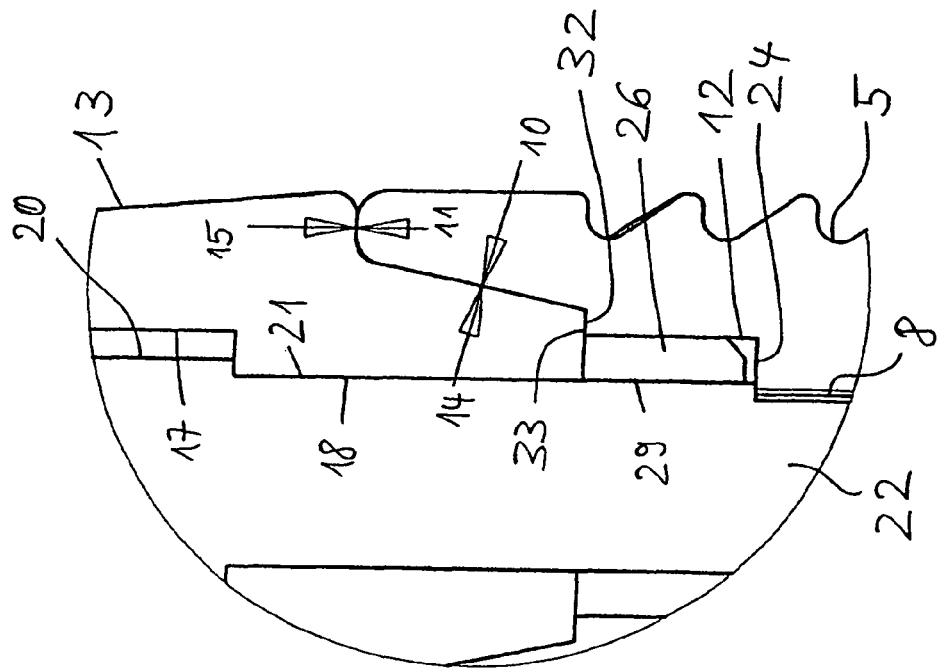
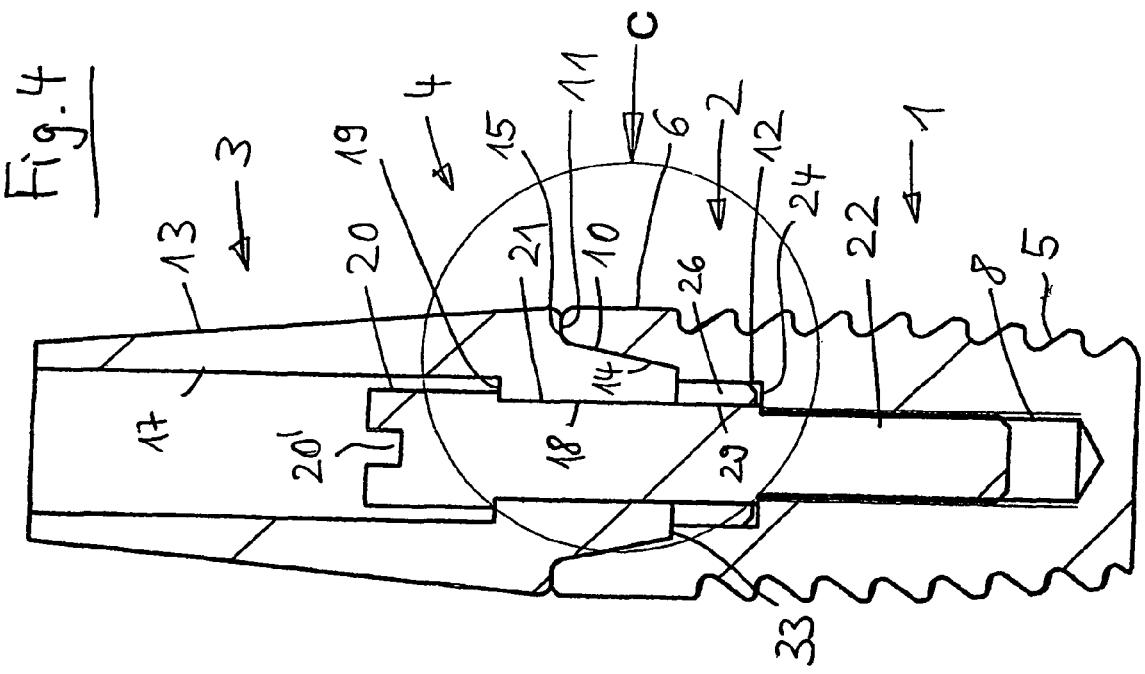

DENTAL IMPLANT

BACKGROUND OF THE INVENTION

This invention relates to a dental implant which comprises an implant screw, an implant abutment and a tightening screw. The implant screw has an external thread with which it can be screwed into a jawbone. The implant abutment is joined with the implant screw and attached to the implant screw by the tightening screw. To the implant abutment, a dental prosthesis, a crown, a tooth cap or the like is directly or indirectly attachable or attached. The tightening screw is screwable or screwed into the implant screw. By the tightening screw, the implant abutment is connectable or connected with the implant screw. With a contact surface, the implant screw rests against a contact surface of the implant abutment.

Such dental implant is known from EP 1 529 498 A1. In one embodiment of EP 1 529 498 A1, the implant screw has a conical contact surface and the implant abutment has a conical contact surface complementary thereto. The relative angular position between the implant screw and the implant abutment is not fixed in this embodiment.

Another embodiment from EP 1 529 498 A1 comprises an implant screw which includes an internal hexagon into which a corresponding external hexagon of the implant abutment engages, so that the implant abutment is held in the implant screw secured against rotation and in a predetermined angular position.

From EP 1 269 932 A1 a dental implant abutment with an implant screw made of metal, namely titanium, and an implant abutment made of ceramics is known. The implant screw and the implant abutment are connected with each other by a metallic connecting piece.

From WO 01/50977 A1 another dental implant is known.

WO 2009/009909 A1 discloses a dental implant with an implant screw and an implant abutment, which are screwed to each other and additionally bonded to each other. This adhesive bond leads to considerable shortcomings both in clinical use and as regards the long-term prognosis of the entire system. On the one hand, it is extremely difficult, if not impossible, to reliably remove the leaking excess adhesive after bonding. Such excess adhesive can lead to inflammations at the implant site and consequently to the implant loss. On the other hand, it sometimes is required to again separate the connection between the implant screw and the implant abutment after inserting the restoration, which after adhesively bonding the two components only is possible with difficulty or not at all. Moreover, the durability of an adhesive in the oral environment is only very difficult to predict. Changes in temperature, fluctuations of the pH value, mechanical loads and moisture lead to rapid aging in particular of formerly plastic materials.

DE 101 29 684 B4 shows another dental implant.

The design of the implant screw and/or the implant abutment can lead to the fact that with certain materials, in particular with ceramics or a ceramic-like material or a material which contains ceramics or a ceramic-like material, but also with materials which contain plastics, extensive material accumulations are present in various regions of these components. Due to these different volumes of material it can occur that the finished component is not sufficiently dimensionally accurate. This risk in particular exists when the manufacturing method includes a shrinking process, as is the case in particular when sintering ceramics or materials containing ceramics, but possibly also with materials which contain plastics. In general, the shrinking process does not proceed linearly in particular during sintering. The material of the implant screw and/or the implant abutment thus each can shrink to a different extent in various regions of these parts corresponding to the different volumes of material. When the implant screw and the implant abutment are joined and braced with each other by the tightening screw, it is therefore not possible to achieve a completely stressfree form fit of the joined surfaces. This results in a risk of fracture and/or the risk of a lack of bacteria tightness. These risks also can result from a surface roughness of the material independent of the shrinking process mentioned above.

In experiments known from the prior art, ceramic contact surfaces have led to far-reaching problems. Production-related inaccuracies, even in the micrometer range, have led to the occurrence of force and stress peaks in the material during the introduction of forces. Other than in metallic components, which have a certain elasticity or ductility due to the material used, ceramic materials are brittle, hardly elastic and more or less not deformable. With the manufacturing methods employed so far, the accuracy of the connection merely could be increased to a certain degree. In microscopic terms, however, this cannot be referred to as a "flat, homogeneous" contact surface. So far, the same rather is present sporadically, approximately comparable to a sand grain under a glass plate lying flat on a surface. This results in stress peaks and resulting fractures of one or both components already with physiologically occurring chewing forces.

SUMMARY OF THE INVENTION

It is the object of the invention to propose an improved dental implant.

In accordance with the invention, this object is solved by the features herein. The dental implant comprises an implant screw with an external thread, an implant abutment and a tightening screw which can be screwed into the implant screw and by which the implant abutment is connectable or connected with the implant screw. With a contact surface, the implant screw rests against a contact surface of the implant abutment. The implant screw and the implant abutment are made of a ceramic material. They are made of a ceramic material at least in the region of their contact surfaces. Advantageously, the implant screw and/or the implant abutment are completely made of a ceramic material.

The contact surface of the implant screw and the contact surface of the implant abutment are ground in against each other. The contact surfaces in particular can be ground in against each other, until they form a form fit.

The invention provides for realizing a two-part dental implant, i.e. a dental implant with an implant screw and an implant abutment, as a fully ceramic dental implant. This means that both the implant screw and the implant abutment (the abutment) are made of a ceramic material. For joining the implant screw and the implant abutment, no metallic components are required, apart from the implant screw. At least the contact surfaces of the implant screw and the implant abutment are made of ceramics.

The form fit of the contact surfaces made of ceramics is achieved in that the contact surfaces are ground in against each other. In this way, a homogeneous and flat abutment interface is obtained, in which no production-related stresses can occur in the material, so that the stability of the entire construction is improved decisively.

The manufacture of the dental implant preferably is carried out by way of the so-called mating, in which a particular implant screw and a particular implant abutment are ground in against each other by means of a suitable grinding means. By means of this method, all geometry errors, which can generate stresses and with a corresponding load can lead to fracture, can be eliminated, and an absolute form fit of the implant screw and the implant abutment can be achieved.

Advantageous developments are described herein.

Advantageously, the contact surface of the implant screw and the contact surface of the implant abutment are conical contact surfaces.

Instead or in addition, however, it is also possible that the contact surface of the implant screw is an axial contact surface and/or a further axial contact surface and/or that the contact surface of the implant abutment is an axial contact surface and/or a further axial contact surface. When in a dental implant such as that according to EP 1 529 498 A1 all occurring forces between the implant screw and the implant abutment are transmitted by conical contact surfaces, this can lead to the fact that in the case of an axial load exerted by the tightening screw and/or by external forces produced when chewing etc. radial forces are produced, which are amplified correspondingly by the conical contact angle and which can lead to the fracture of the dental implant. This risk is all the greater, when the implant screw and/or the implant abutment are made of brittle materials such as ceramics, which only have a low elongation at break. When axial contact surfaces are present, axial forces which act on the dental implant can at least also be transmitted via the axial contact surfaces, which leads to a relief of the conical contact surfaces. As a result, the risk of fracture under axial loads of the dental implant is reduced or eliminated.

Advantageously, the axial contact surfaces are provided at one end of the conical contact surfaces.

According to a further advantageous development, axial contact surfaces are provided at both ends of the conical contact surfaces.

According to a further advantageous development, the dental implant comprises a positioning bushing, which is non-rotatably mountable or mounted in the implant screw and with which the implant abutment is non-rotatably connectable or connected. In this solution, the implant screw and the implant abutment initially can rotate against each other, so that in particular in the method of mating these parts can be ground in against each other. Thereafter, the positioning bushing is inserted, which positions the implant screw and the implant abutment secured against rotation relative to each other.

The positioning bushing can have a non-rotatable outer surface. Correspondingly, the implant screw can have a non-rotatable inner surface. The non-rotatable outer surface and the non-rotatable inner surface preferably are complementary to each other. All surfaces which effect a securement against rotation are suitable here. In particular, the non-rotatable outer surface can be formed as an external hexagon. In this case, the non-rotatable inner surface can be formed as a preferably complementary internal hexagon. It is, however, also possible that instead of a hexagon a square, an octagon or a cross-section with another regular or irregular polygon is used.

Another advantageous development is characterized in that the positioning bushing includes a protrusion and the implant abutment includes a cutout complementary thereto. The protrusion preferably is formed as web. The cutout preferably is formed as groove. The reverse arrangement can, however, also be used, in which the positioning bushing includes a cutout, in particular a groove, and the implant abutment includes a protrusion complementary thereto, in particular a web.

Advantageously, the protrusion or the web and the cutout or the groove are formed conically. This can ensure an even better positioning. In particular, a complete protection against rotation thereby can be made possible more easily or at all. This protection against rotation prevents any production-related rotation. On the one hand, this is achieved or promoted by the conically formed, oblique, i.e. non-parallel-walled surfaces between the positioning bushing and the implant abutment. It is furthermore achieved or promoted by the fact that the protection against rotation is realized by a separate part, namely the positioning bushing, which is firmly connected neither with the implant screw nor with the implant abutment. This allows that the corresponding inclined surfaces between the positioning bushing and the implant abutment correspond with each other not in the apical, i.e. bottommost end position of the implant abutment, but already earlier. Thus, a reproducible zero-degree rotation is accomplished, which is important in particular in constructions in which several implants are connected with each other, in particular in bridges.

The invention furthermore relates to a method for manufacturing a dental implant according to the invention. The method according to the invention is characterized in that a contact surface of the implant screw and a contact surface of the implant abutment are ground in against each other.

An advantageous development of this method is characterized in that a conical contact surface of the implant screw and a conical contact surface of the implant abutment are ground in against each other. Instead or in addition, an axial contact surface of the implant screw and an axial contact surface of the implant abutment can be ground in against each other and/or a further axial contact surface of the implant screw and a further axial contact surface of the implant abutment can be ground in against each other.

Advantageously, one or more or all contact surfaces are ground in against each other, until they form a form fit.

BRIEF DESCRIPTION OF THE DRAWINGS

Exemplary embodiments of the invention will be explained in detail below with reference to the attached drawing, in which:

FIG. 2 shows the parts of the dental implant of FIG. 1 in a side view, FIG. 3 shows the parts of the dental implant of FIGS. 1 and 2 in a lateral sectional view, FIG. 4 shows a modified embodiment of the dental implant of FIGS. 1 to 3 in the mounted condition in a lateral sectional view, and FIG. 5 shows the detail "C" of FIG. 4 in an enlarged representation.

DESCRIPTION OF THE PREFERRED EMBODIMENTS

Figure 1:
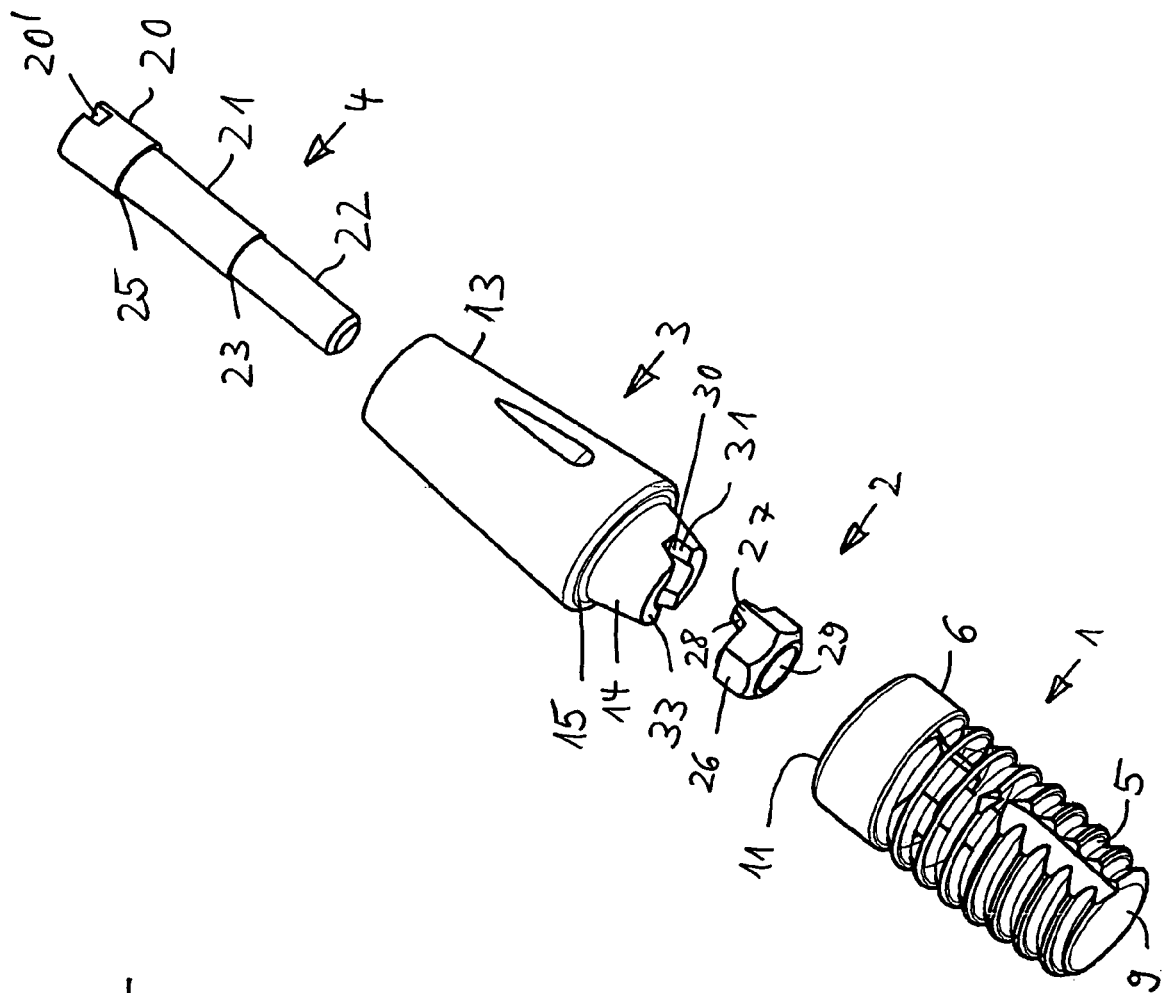
FIG. 1 shows a dental implant, consisting of an implant screw, a positioning bushing, an implant abutment, and a tightening screw in the demounted condition in a perspective view.

The dental implant shown in the drawing comprises an implant screw 1, a positioning bushing 2, an implant abutment 3 and a tightening screw 4.

The implant screw 1 is made of a ceramic material. It includes an external thread 5, with which it can be screwed into a jawbone, and a cylindrical region 6 which is provided at the end of the implant screw 1 facing the implant abutment 3. In general, the cylindrical region 6 partly protrudes from the jawbone in the condition of the implant screw 1 screwed in. Its outside diameter corresponds to the largest outside diameter of the implant abutment 3.

The implant screw 1 furthermore includes an inner blind hole 7. The inner blind hole comprises an internal thread 8 into which the tightening screw 4 can be screwed. The internal thread 8 extends approximately down to the lower end face 9 of the implant screw 1. Furthermore, the inner blind hole 7 comprises a conical contact surface 10 which is open towards the upper end face of the implant screw 1 and which conically broadens towards the upper end face. The upper end face of the implant screw 1 forms an axial contact surface 11. The axial contact surface 11 is a ring surface.

The conical contact surface 10 is downwardly adjoined by a non-rotatable inner surface 12. The non-rotatable inner surface 12 is formed as internal hexagon. The diagonal of the internal hexagon corresponds to the diameter at the lower end of the conical contact surface 10.

The implant abutment 3 is made of a ceramic material. In includes an outer conical shell surface 13, which extends to the top. To the outer conical shell surface 13 a dental prosthesis or the like can be attached. The implant abutment 3 furthermore includes a conical contact surface 14, which tapers towards the lower end of the implant abutment 3. The conical contact surface 14 of the implant abutment 3 is complementary to the conical contact surface 10 of the implant screw 1.

The upper end of the conical contact surface 14 of the implant abutment 3 is adjoined by a shoulder surface pointing to the outside, which forms an axial contact surface 15. The axial contact surface 15 furthermore extends from the lower end of the outer conical shell surface 13 to the inside. It is a ring surface.

The lower end of the conical contact surface 14 of the implant abutment 3 is adjoined by the lower end face of the implant abutment 3 pointing to the inside, which forms a further axial contact surface 33. It is a ring surface.

The implant abutment 3 includes a through hole 16 which comprises an upper region 17 greater in diameter and a lower region 18 smaller in diameter, which are separated from each other by a shoulder 19.

The tightening screw 4 is made of metal. It comprises a head 20, a shaft 21 adjoining thereto and a thread part 22 adjoining thereto. The thread part 22 of the tightening screw 4 can be screwed into the internal thread 8 of the implant screw 1. The end of the thread part 22 facing the shaft 21 is designated with 23. The head 20 of the tightening screw 4 has a greater diameter than its shaft 21. In the mounted condition, the shoulder 25 formed thereby rests on the shoulder 19 in the through hole 16 of the implant abutment 3. The shoulder 25 is braced against the shoulder 19. In the head 20 a slot 20' or a receptacle of some other shape is provided, into which a tool can engage, for example a screw driver.

Before mounting the dental implant, the conical contact surface 10 of the implant screw 1 and the conical contact surface 14 of the implant abutment 3 are ground in against each other by way of mating. In this process, the implant screw 1 and the implant abutment 3 are rotated relative to each other. By grinding in, absence of stress and bacteria tightness are achieved. Advantageously, the conical contact surfaces 10 and 14 are ground in against each other, until they form a form fit.

Furthermore, it is advantageous when the conical contact surfaces 10 and 14 are ground in against each other, until the axial contact surface 11 of the implant screw 1 and the axial end face 15 of the implant abutment 3 rest against each other and form a form fit. The absence of stress and the bacteria tightness are further improved thereby.

After grinding in, the implant screw 1 and the implant abutment 3 are separated from each other. Into the implant screw 1, the positioning bushing 2 is inserted. The positioning bushing 2 is non-rotatably mounted in the non-rotatable inner surface 12 of the implant screw 1 formed as internal hexagon. For this purpose, the positioning bushing 2 has a non-rotatable outer surface 26 formed as external hexagon. The internal hexagon of the non-rotatable inner surface 12 corresponds to the external hexagon of the non-rotatable outer surface 26.

Furthermore, the positioning bushing 2 has a protrusion 27 at is upper end, which is directed upwards, i.e. towards the implant abutment 3. The protrusion 27 is formed as web. It has conical outer surfaces 28.

The positioning bushing 2 furthermore includes a through hole 29 through which the shaft 21 of the tightening screw 4 can be put. The protrusion 27 formed as web merely is located at a point of the upper ring surface of the positioning bushing 2. On the opposite side of the upper ring surface of the positioning bushing 2, however, a further corresponding protrusion might be located.

The implant abutment 3 has a cutout 30 complementary to the protrusion 27 formed as web. The cutout 30 is formed as groove. It has conical outer surfaces 31 which correspond to the conical outer surfaces 28 of the protrusion 27 of the positioning bushing 2 formed as web. The cutout 30 is located at the lower end of the implant abutment 3 facing the implant screw 1. As shown in FIG. 1, two cutouts 30 aligned with each other are present in the lower ring surface 33 of the implant abutment 3. It would, however, also be sufficient to have only one cutout 30.

The axial contact surface 11, which is formed by the upper end face of the implant screw 1, is rounded towards the conical contact surface 10. Furthermore, the axial contact surface 11 also is rounded towards the cylindrical region 6. The axial contact surface 15, which is formed by the shoulder surface at the upper end of the conical contact surface 14, is rounded towards the conical contact surface 14. Furthermore, the axial contact surface 15 also is rounded towards the outer conical shell surface 13. Both the axial contact surface 11 and the axial contact surface 15 each extend in radial direction. Thus, the surface normals of the axial contact surface 11 and the axial contact surface 15 each extend in longitudinal direction of the dental implant.

In the modified embodiment of FIGS. 4 and 5, parts which correspond with those of the embodiment of FIGS. 1 to 3 are provided with the same reference numerals. These parts will not be described again.

In addition to the embodiment of FIGS. 1 to 3, further axial contact surfaces are present in the modification of FIGS. 4 and 5. The further axial contact surface 32 of the implant screw 1 is formed by a shoulder which adjoins the lower end of the conical contact surface 10 and from there extends radially to the inside. The further axial contact surface 33 of the implant abutment 3 is formed by the lower end face of the implant abutment 3, which adjoins the lower end of the conical contact surface 14 and from there extends radially to the inside.

The conical contact surfaces 10 and 14 preferably are ground in against each other, until the axial contact surfaces 11, 15 and the further axial contact surfaces 32, 33 rest against each other and form a form fit. The absence of stress and the bacteria tightness are further improved thereby.

During assembly of the dental implant, the positioning bushing 2 is inserted into the non-rotatable inner surface 12 of the implant screw 1 formed as internal hexagon. Subsequently, the conical contact surface 14 of the implant abutment 3 is positioned at the conical contact surface 10 of the implant screw 1. In doing so, the implant abutment 3 is positioned such that the protrusion 27 of the positioning bushing 2 enters into the cutout 30 of the implant abutment 3 and comes to lie there. Finally, the tightening screw 4 is put through the through hole 16 of the implant abutment 3 and through the through hole 29 of the positioning bushing 2 and screwed to the internal thread 8 of the implant screw 1, whereby the mounted position shown in FIGS. 4 and 5 is reached. The implant screw 1 and the implant abutment 3 then are axially and radially fixed to each other.

The invention claimed is:

1. A dental implant, comprising an implant screw (1) with an external thread (5), an implant abutment (3) and a tightening screw (4) which can be screwed into the implant screw (1) and by which the implant abutment (3) is connectable or connected with the implant screw (1), wherein the implant screw (1) rests against a contact surface (14, 15, 33) of the implant abutment (3) with a contact surface (10, 11, 32), the contact surfaces (10, 11, 32; 14, 15, 33) of the implant screw (1) and the implant abutment (3) are both made of a ceramic material at all locations of contact, a homogeneous and flat abutment interface is formed at all said locations of contact between the contact surface (10, 11, 32) of the implant screw (1) and the contact surface (14, 15, 33) of the implant abutment (3) with a form fit, the contact surface of the implant screw (1) comprises a conical contact surface (10) and radially-extending contact surfaces (11, 32) directly located at opposite ends of the conical contact surface (10), the contact surface of the implant abutment (3) comprises a conical contact surface (14) and radially-extending contact surfaces (15, 33) directly located at opposite ends of the conical contact surface (14), with one (33) of said radially-extending contact surfaces (15,33) forming a flat end of both said conical contact surface (14) and said abutment (3), and with the radially-extending contact surfaces (11, 15; 32, 33) resting against one another in a form fit at all said locations of contact therebetween and the conical contact surfaces (10, 14) resting against one another in a form fit between said radially-extending contact surfaces (11, 15; 32, 33) and over the complete length of both said conical contact surfaces (10, 14), the dental implant having a positioning bushing (2) which is non-rotatably mountable or mounted in the implant screw (1) and with which the implant abutment (3) is non-rotatably connectable or connected, with said radially-extending contact surface (33) forming the flat end of said conical contact surface (14) and abutment (13) resting on top of an upper end of said bushing (2) and against the respective radially-extending contact surface (32) of the implant screw (1) over the length of the radially-extending contact surface (33) forming the flat end of said conical contact surface (14) and abutment (3).

2. The dental implant according to claim 1, wherein the positioning bushing (2) has a non-rotatable outer surface (26) and the implant screw (1) has a non-rotatable inner surface (12).

3. The dental implant according to claim 2, wherein the non-rotatable outer and inner surfaces (26, 12) are respectively external and internal hexagons.

4. The dental implant according to claim 1, wherein the positioning bushing (2) has an axially-extending protrusion (27) above an upper radial end surface thereof and the implant abutment (3) has a cutout (30) extending axially inwardly of a lower radially-extending contact surface (33) thereof and complementary to the protrusion (27).

5. The dental implant according to claim 4, wherein the protrusion (27) and the cutout (30) are formed conically.

6. The dental implant according to claim 4, wherein the protrusion (27) is a web and the cutout (30) is a groove.

7. The dental implant according to claim 1, wherein the conical contact surface (14) of the abutment (3) tapers towards a lower end thereof, the abutment (3) additionally comprises an outer conical shell surface (13) tapering in an opposite direction from the conical contact surface (14) and the screw (1) comprises a cylindrical region (6) facing the implant abutment (3).

8. The dental implant according to claim 7, wherein one (11) of the radially-extending contact surfaces (11, 32) of the implant screw (1) is formed at an upper end of the implant screw (1) and rounded towards the inner conical contact surface (10) and outer cylindrical region (6) thereof and the radially-extending contact surface (15) of the abutment (3) at the end of the conical contact surface (14) opposite the end (33) of the conical contact surface forming the flat end of both the conical contact surface (14) and abutment (3), being rounded towards both the conical contact surface (14) and outer conical shell surface (13) thereof.

9. The dental implant according to claim 1, wherein the abutment (3) comprises a through-hole (16) in turn comprising an upper region (17) having a first diameter, a lower region (18) having a second diameter, the first diameter being greater than the second diameter, and a radially-extending shoulder (19) adjoining the upper and tower regions (17, 18) and extending perpendicular to an axis of the abutment (3).

10. The dental implant according to claim 9, wherein the implant screw (1) comprises an inner blind hole (7) having an internal thread (8), and the tightening screw (4) comprises a head (20), a shaft (21) adjoining the head (20) at a shoulder (25) and a thread part (22) adjoining the shaft (21) at an end (23) facing the shaft (21), with the head (20) having a greater diameter than the shaft (21) and, in mounted co edition, the shoulder (25) resting on the shoulder (19) in the through-hole (16) of the implant abutment (3) and braced thereagainst.

11. A method for manufacturing a dental implant according to claim 1, wherein a contact surface (10, 11, 32) of the implant screw (1) and a contact surface (14, 15, 33) of the implant abutment (3) are ground in against each other.

12. The method according to claim 11, wherein a conical contact surface (10) of the implant screw (1) and a conical contact surface (14) of the implant abutment (3) are ground in against each other and/or an axial contact surface (11) of the implant screw (1) and an axial contact surface (15) of the implant abutment (3) are ground in against each other and/or a further axial contact surface (32) of the implant screw (1) and a further axial contact surface (33) of the implant abutment (3) are ground in against each other.

13. The method according to claim 11, wherein one or more or all contact surfaces (10, 11, 32; 14, 15, 33) are ground in against each other, until they form a form fit.

* * * * *